US011433030B2

(12) United States Patent
Stella et al.

(10) Patent No.: US 11,433,030 B2
(45) Date of Patent: *Sep. 6, 2022

(54) EXTENDED RELIEF DOSAGE FORM

(71) Applicant: The Procter & Gamble Company, Cincinnati, OH (US)

(72) Inventors: Mark Edward Stella, Cincinnati, OH (US); John Richard Entwisle, Mason, OH (US); Baltej Ludher, Cincinnati, OH (US); Jonathan E. Clark, Loveland, OH (US); Daren K. Anness, Loveland, OH (US); Guhan Balan, Mason, OH (US); Andrew Nicholas Carr, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/714,856

(22) Filed: Dec. 16, 2019

(65) Prior Publication Data

US 2020/0113841 A1    Apr. 16, 2020

Related U.S. Application Data

(63) Continuation of application No. 15/713,746, filed on Sep. 25, 2017, now Pat. No. 10,576,041.

(60) Provisional application No. 62/399,511, filed on Sep. 26, 2016.

(51) Int. Cl.
| *A61K 9/20* | (2006.01) |
| *A61K 9/24* | (2006.01) |
| *A61K 9/00* | (2006.01) |
| *A61K 9/48* | (2006.01) |
| *A61K 31/137* | (2006.01) |
| *A61K 31/192* | (2006.01) |
| *A61K 31/485* | (2006.01) |

(52) U.S. Cl.
CPC .......... *A61K 9/2086* (2013.01); *A61K 9/0002* (2013.01); *A61K 9/2004* (2013.01); *A61K 9/209* (2013.01); *A61K 9/2054* (2013.01); *A61K 9/2095* (2013.01); *A61K 9/4808* (2013.01); *A61K 31/137* (2013.01); *A61K 31/192* (2013.01); *A61K 31/485* (2013.01); *A61K 2300/00* (2013.01)

(58) Field of Classification Search
CPC .................................................. A61K 9/2086
See application file for complete search history.

(56) References Cited

U.S. PATENT DOCUMENTS

| 4,552,899 A | 11/1985 | Sunshine et al. |
| 5,681,577 A * | 10/1997 | Lech .......... A61P 37/08 424/439 |
| 5,859,060 A | 1/1999 | Platt |
| 7,863,287 B2 | 1/2011 | Berlin |
| 8,246,988 B2 | 8/2012 | Kamath et al. |
| 8,252,330 B2 | 8/2012 | Kamath et al. |
| 10,576,041 B2 | 3/2020 | Stella et al. |
| 2003/0175336 A1 | 9/2003 | Luber et al. |
| 2004/0097536 A1 | 5/2004 | Cho |
| 2005/0249802 A1 | 11/2005 | Khanolkar et al. |
| 2005/0261280 A1 | 11/2005 | Munayyer et al. |
| 2005/0266032 A1 | 12/2005 | Srinivasan et al. |
| 2006/0062847 A1 | 3/2006 | Kolter et al. |
| 2007/0003621 A1 * | 1/2007 | Nangia ................ A61K 9/1652 424/469 |
| 2008/0014274 A1 | 1/2008 | Bubnis |
| 2008/0026055 A1 | 1/2008 | Fubara et al. |
| 2008/0260824 A1 | 10/2008 | Nangia et al. |
| 2008/0311201 A1 | 12/2008 | Der-yang et al. |
| 2009/0082316 A1 | 3/2009 | Cimiluca et al. |
| 2010/0078541 A1 | 4/2010 | Fathi |
| 2010/0172984 A1 | 7/2010 | Padhi |
| 2012/0207831 A1 | 8/2012 | Stella et al. |
| 2016/0175454 A1 | 6/2016 | Ghebre-Sellassie et al. |
| 2017/0100355 A1 | 4/2017 | Cavatur et al. |

(Continued)

FOREIGN PATENT DOCUMENTS

| AU | 8919898 A | 3/2000 |
| EP | 0180597 B1 | 3/1992 |
| WO | 9507103 A1 | 3/1995 |

(Continued)

OTHER PUBLICATIONS

Phadtare et al., "Hypromellose—a choice of polymer in extended release tablet formulation", WJPPS, 2014, vol. 3, Iss 9, 551-566. (Year: 2014).*
All Office Actions; U.S. Appl. No. 15/713,746.
All Office Actions; U.S. Appl. No. 16/714,856.
Carrick, David et al., "The separation and analysis of pseudoephedrine-hydrochloride and diphenhydramine hydrochloride from process and degradation products", Abstracts, 36th Middle Atlantic Regional Meeting of the American Chemical Society, Jun. 8-11, 2003, 373.

(Continued)

*Primary Examiner* — Gina C Justice
(74) *Attorney, Agent, or Firm* — Jason J. Camp

(57) ABSTRACT

A dosage form with a first portion and a second portion. The first portion can be an immediate release portion and can comprise a pain reliever, which can be naproxen or naproxen sodium. The second portion can be an extended release portion and can comprise pseudoephedrine or a pharmaceutically acceptable salt thereof and/or dextromethorphan or a pharmaceutically acceptable salt thereof. The dosage form can optionally comprise a stabilizing agent. The dosage form can be adapted to maintain a therapeutically effective amount of pain reliever, pseudoephedrine, or a pharmaceutically acceptable salt thereof, and/or dextromethorphan, or a pharmaceutically acceptable salt thereof, for at least eight hours.

19 Claims, 4 Drawing Sheets

(56) References Cited

U.S. PATENT DOCUMENTS

| | | |
|---|---|---|
| 2018/0085317 A1 | 3/2018 | Stella |
| 2020/0113841 A1 | 4/2020 | Stella et al. |

FOREIGN PATENT DOCUMENTS

| | | | |
|---|---|---|---|
| WO | 2003026626 A2 | 4/2003 | |
| WO | 2007072503 A2 | 6/2007 | |
| WO | 2010078541 A1 | 7/2010 | |
| WO | WO-2010078541 A1 * | 7/2010 | ........... A61K 9/2081 |
| WO | 2016063057 A1 | 4/2016 | |

OTHER PUBLICATIONS

International Search Report and Written Opinion; Application Ser. No. PCT/US2017/053157; dated Nov. 15, 2017, 14 pages.

Perez, Loudes et al., "Stability indicating assay of pseudoephedrine hydrochloride tablets", Abstracts, 36th Middle Atlantic Regional Meeting of the American Chemical Society, dated Jun. 8-11, 2003, 278.

Phadtare, Dipti et al. "Hypromellose—A Choise of Polymer In Extended Release Tablet Formulation", Worldl Journal of Pharmacy and Pharmaceutical Sciences, vol. 3, Issue 9, pp. 551-566, 2014.

PUZ_"Use of antioxidant BHT in asymmetric membrane tablet coatings to stabilize the core to the acid catalyzed peroxide oxidation of a tioether drug", MEDLINE, Jan. 1, 2005, whole document.

Shin, Chui et al. "Simplified HPLC Method for the Determination of Pseudoephedrine Hydrochloride from Allegra D. Tablet", The Journal Of Applied Pharmacology, 15, 123-126 , 2007.

Wu, Nian, "Quantitative and structural determination of pseudoephedrine sulfate and its related compounds in pharmaceutical preparations using high-performance liquid chromatography", Journal of Pharmaceutical and Biomedical Analysis 30 (2002) 1143-1155.

* cited by examiner

EXTENDED RELIEF DOSAGE FORM

FIELD OF THE INVENTION

The present invention is generally related to an extended relief dosage form and more particularly, a stable extended relief dosage form that contains a pain reliever, a decongestant, and an antitussive.

BACKGROUND OF THE INVENTION

Typical symptoms experienced by those suffering from an upper respiratory tract infection such as the common cold or flu can include nasal congestion, runny nose, sneezing, headache, dry cough, sore throat, sinus pressure or pain, chest congestion, muscle aches/pains, wet/chesty cough, fever, and combinations thereof. As a result, many multiple symptom relief (MSR) products have been developed to treat a variety of these symptoms simultaneously.

For optimal efficacy, many MSR products must be taken every four to six hours. However, it would be desirable for an MSR product to deliver symptom relief over a longer period of time. An extended relief product can be more convenient for consumers and can improve dosing compliance, which can ultimately enhance the overall effectiveness of the product.

One problem with developing an extended relief MSR product is that each active has a different duration of action and pharmacokinetic behavior in the human body. For instance, the half-life of immediate release naproxen sodium (NAP) is 12-24 hours, the half-life of immediate release pseudoephedrine hydrochloride (PSE) is 4.3-8 hours, and the half-life of immediate release dextromethorphan hydrobromide (DXM) is 3-5 hours. Matching the duration of action for each active over an extended time period, for instance 8 or 12 hours, within a single dosage form requires modification of the release characteristics for each active and significant tailoring of the dose form through the use of immediate, extended, delayed or mixed release formulation technologies. Furthermore, when NAP, PSE and DXM are combined in one dosage form, the PK profile of the immediate release NAP and the extended release PSE and DXM can be different than if the actives are used alone or in combination with just one other active due to interactions between excipients and/or actives.

In addition, it is difficult to formulate a stable MSR product because some actives can undergo an oxidation reaction due to the interaction with excipients and certain processing conditions, resulting in the formation of unwanted degradation products.

As such, there remains a need in the area of over-the-counter (OTC) drugs for improved options for the treatment of symptoms associated with the common cold, influenza, or respiratory allergies. In particular, there is a need for a stable, convenient and highly effective MSR product that comprises a pain reliever, a decongestant, and an antitussive in a dosage form that provides relief over an extended period of time.

SUMMARY OF THE INVENTION

A dosage form comprising: (a) a first portion comprising naproxen or a pharmaceutically acceptable salt thereof; wherein the first portion is an immediate release portion; and (b) a second portion comprising pseudoephedrine or a pharmaceutically acceptable salt thereof and dextromethorphan or a pharmaceutically acceptable salt thereof; wherein the second portion is an extended release portion; wherein the dosage form is adapted to reach greater than 65% dissolution of dextromethorphan within 3 hours, greater than 75% dissolution of pseudoephedrine within 2 hours, and greater than 80% dissolution of naproxen within 30 minutes as measured by the Dissolution Method.

A dosage form comprising: (a) a first portion comprising a pain reliever selected from the group consisting of acetaminophen, ibuprofen, ketoprofen, diclofenac, aspirin, naproxen, pharmaceutically acceptable salts thereof, and combinations thereof; (b) a second portion comprising pseudoephedrine or a pharmaceutically acceptable salt thereof; wherein the second portion is an extended release portion; and (c) from about 0.01% to about 8% of a chelating agent; wherein the dosage form comprises less than about 0.01%, by weight of the dosage form, methcathinone.

A method of improving the stability of a dosage form comprising the steps of: (a) granulating a first mixture comprising a pain reliever to form a plurality of first portion granules; (b) blending the plurality of first portion granules with a first portion excipient to form an immediate release mixture; (c) blending a second mixture comprising pseudoephedrine or a pharmaceutically acceptable salt thereof, dextromethorphan or a pharmaceutically acceptable salt thereof, and an extended release polymer; (d) adding a stabilizing agent and mixing to form a plurality of second portion granules; (e) blending the second portion granules with a second portion excipient to form an extended release mixture; wherein the extended release mixture comprises less than about 0.01% methcathinone; and (f) forming a dosage form comprising a first layer of the immediate release mixture and a second layer of the extended release mixture.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Dosage forms that can be consumed every twelve hours are known. However, it is difficult to make a dosage form comprising a pain reliever, a decongestant, and an antitussive that provides therapeutic relief for the entire twelve hour dosage interval. In addition, it is difficult to formulate a stable MSR product with PSE and DXM because these actives can degrade, resulting in a reduced level of active in the product and the presence of unwanted degradants.

Figure 1A:
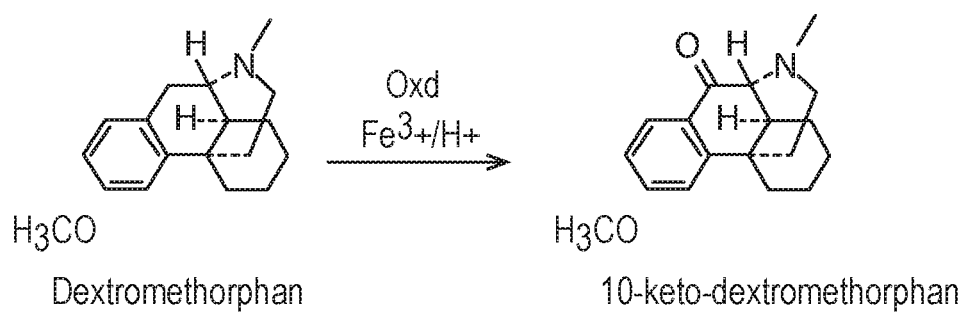
FIG. 1A shows the degradation pathway of dextromethorphan.
Figure 1B:
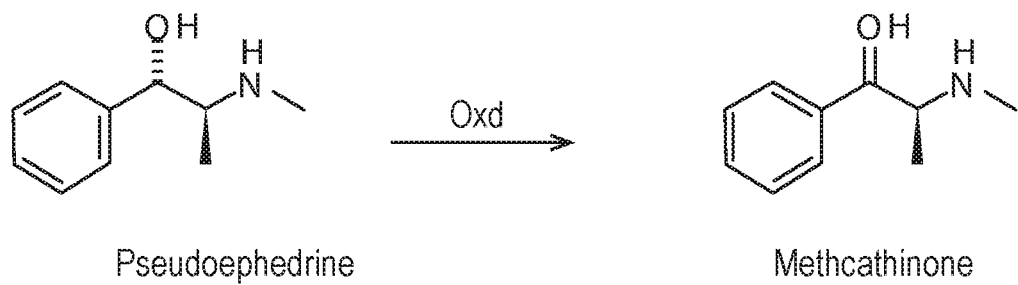
FIG. 1B shows the degradation pathway of pseudoephedrine.

It was found that the presence of catalysts (i.e. iron and/or peroxides), heat, air flow, pH, and/or oxygen can trigger the oxidation of PSE and/or DXM. FIG. 1A shows the degradation pathway of DXM, in which DXM can form 10-keto-dextromethorphan in the presence of $Fe^{3+}$ and $H^+$. FIG. 1B shows the degradation pathway of PSE, in which PSE can form methcathinone.

Methcathinone is listed as a Schedule I controlled substance by the United States Controlled Substances Act (21 CFR § 1308.11(f)(5)). The methcathinone degradation product is known to exist in some current PSE containing products, with the level of methcathinone present listed on the monograph as 0.2%. However, it has been found that the level of methcathinone degradation product in a PSE-containing dosage form can now be reduced to a non-detectable level.

In order to provide therapeutic relief for the entire dosage interval and minimize the production of PSE and DXM degradation products, the dosage form can be a bi-layer tablet comprising two portions, the first portion can be an immediate release (IR) portion comprising NAP and the second portion can be an extended release (ER) portion comprising DXM, PSE, and a stabilizing agent. In another aspect, the bi-layer tablet can comprise an immediate release portion comprising NAP and DXM and an extended release portion comprising PSE and a stabilizing agent. In another aspect, the immediate release portion is essentially free of DXM. In another aspect, the dosage form can be adapted to maintain a therapeutically effective amount of NAP, DXM, and/or PSE for at least twelve hours, alternatively for at least eight hours.

It has been found that the oxidation of PSE and DXM can be overcome by the addition of at least one stabilizing agent. In one aspect, the stabilizing agent can be a chelating agent. Alternatively, the stabilizing agent can be an antioxidant. While not wishing to be bound by theory, it is believed that the chelating agent can bind the metal ions present in the formula or introduced during processing and the antioxidant can bind free radicals, thus minimizing the oxidation of PSE and DXM. In one aspect, the dosage form is substantially free of methcathinone and/or 10-keto-dextromethorphan degradation products.

The present invention further relates to a method of reducing the level of methcathinone and/or 10-keto-dextromethorphan degradation products in a dosage form containing PSE and/or DXM. It has been found that modifying the processing steps to remove heat and/or water during the formation of the dosage form can also reduce the oxidation of PSE and/or DEX.

As used herein, "active" refers to an active ingredient or an active moiety.

As used herein, "AUC" refers to the area under the concentration-time curve from time of dosing up to a time point, calculated by the linear trapezoidal rule. AUC is a parameter that shows the cumulative plasma concentration of a drug over time, and is an indicator of the total amount and availability of a drug in the plasma. "$AUC_{(0-t)}$" is defined as AUC for any value of time up to t hours. In one example, t is 12 hours (referred to herein as $AUC_{(0-12)}$), other examples can include $AUC_{(0-6)}$ and $AUC_{(0-8)}$. "$AUC_{(0-\infty)}$" is defined as calculated AUC extrapolated to infinity. $AUC_{(0-\infty)}$, is calculated as equal to $AUC_{last}$+Ct/lambda z, wherein $AUC_{last}$ is the AUC until the time point of last measurable concentration, Ct is the last measurable plasma concentration, and lambda z is the terminal phase rate constant. Terminal phase rate constant lambda z is determined from the slope of the drug concentration-time curve using linear regression on terminal data points of the curve.

As used herein "bioequivalence" refers to the absence of a significant difference in the rate and extent to which the active ingredient or active moiety in a dosage form becomes available at the site of drug action when administered at the same molar dose under similar conditions. Two products can be considered bioequivalent if the 90% confidence interval (CI) of the ratio of means between the maximum plasma concentration (Cmax), $AUC_{(0-t)}$ and $AUC_{(0-\infty)}$ of the one or more active(s) in the dosage form relative to one or more reference products for the active(s) of interest is within 80.00% to 125.00%. As used herein "substantially bioequivalent" refers to within 80% of being considered bioequivalent, alternatively within 85%, alternatively within 90%, alternatively within 93%, alternatively within 95%, alternatively within 98%, alternatively within 102%, alternatively within 105%, alternatively within 107%, alternatively within 110%, alternatively within 115%, alternatively within 120% for the upper or lower bounds and/or for the point estimate for the ratio of means.

As used herein "delayed release" refers to a dosage form or a portion of a dosage form that has been deliberately modified such that the majority of the drug active that is contained in or on the dosage form is released or absorbed into the blood plasma some period of time after administration. In one aspect, the delayed release dosage form has an enteric coating, which means that the coating is pH sensitive and the benefit is not experienced by the consumer until the dosage form reaches certain regions of the intestine, specifically, the distal small intestine. One advantage of a delayed release dosage form is that it can be formulated to release an active ingredient after a specified time period or upon encountering the proper environment (for example, release based on pH, enzymatic activity, or solubility). Delayed release stands in contrast to other controlled or modified release dose forms such as extended or prolonged release that deliver an active slowly over an extended duration of time rather than rapidly or immediately after a delay period.

As used herein, "dissolve" or "dissolving" means the process whereby a solid becomes incorporated into a liquid so as to form a solution.

As used herein, "dosage form" refers to a dosage unit containing an amount of a drug active suitable for administration on a single occasion, according to sound medical practice. The dosage form may include a variety of orally administered dosage forms. Non-limiting examples of dosage forms can include liquid formulations including solid particles suspended in a liquid formulation, a solid in a gelatin or foam, or a solid dose in the form of a tablet, capsule, powder, granules, pellets, microspheres, nanospheres, beads, or nonpareils, and combinations thereof. In one aspect, the dosage form is a tablet or a capsule. Dosage forms can be orally administered and are typically swallowed immediately, slowly dissolved in the mouth, or chewed.

As used herein, "extended release" refers to a dosage form that has been deliberately modified wherein the dosage form or a portion of the dosage form is formulated in such a manner as to make the drug active available over an extended period of time following administration.

As used herein, "immediate release" refers to a dosage form or a portion of a dosage form where no deliberate effort has been made to modify the release rate. In the case of capsules, tablets and particles, the inclusion of a disintegrating agent is not interpreted as a modification. Typically, the drug active in an immediate release dosage form will be released into the stomach.

As used herein, "matrix" refers to a dosage form or a portion of a dosage form wherein the active is distributed uniformly within the structure of a suitable material that is used in the production of the dosage form. Suitable materials can include synthetic polymeric materials, cellulosic materials, and inorganic excipients which are commonly used in pharmaceutical formulations.

In one aspect, the materials can be modified by varying the compression forces during tableting, which can change the release rates for the actives. In one aspect, the compression forces are between about 5 kilonewtons (kN) and 50 kN, alternatively between about 10 kN to about 40 kN, alternatively from about 15 kN to about 30 kN.

In one aspect, the materials in the matrix, in particular the polymer, are substantially insensitive to changes in compression force. Choosing a material that is substantially insensitive to changes in compression can simplify manufacturing because this variable does not need to be controlled. In one aspect, the polymers that are substantially insensitive to changes in compression force can be swellable polymers. Non-limiting examples of swellable polymers can include hydroxypropyl methylcellulose (HPMC), hydroxypropyl cellulose, and combinations thereof.

As used herein, "multiple symptom relief" or "MSR" refers to products that contain more than one active that can treat more than one symptom.

As used herein, "PK profile" refers to a pharmacokinetic profile which is the concentration of a drug in plasma over time. From the PK profile one can determine parameters such as Cmax, the concentration at the end of the dosage interval (Cmin), and AUC.

As used herein, "room temperature" refers to temperatures in the range of 20° C. to 25° C.

As used herein, the term "therapeutically effective amount" is an amount of an active that produces the desired therapeutic response upon oral administration. One skilled in the art can readily determine the therapeutically effective amount (e.g., effective blood plasma levels) of a pharmaceutically active agent for a given patient by considering factors such as, for example, the particular active being administered, the bioavailability characteristics of the active, the dose regimen desired, the age and weight of the patient, and the like. In one aspect, the therapeutically effective amount can be determined by matching or comparison of the Cmax, $AUC_{(0-t)}$ and $AUC_{(0-\infty)}$ with one or more reference products containing the active(s) of interest. In another aspect, the therapeutically effective amount can be evaluated by in vivo serum analysis.

The reference product can be a monographed DXM product that is dosed every 4 hours over a 12 hour period, which contains 20 mg or one third the amount of DXM as the dosage form, a monographed DXM that is dosed every 6 hours, which contains 30 mg or one half the amount of DXM as the dosage form, and/or a monographed PSE product that is dosed every 4 hours, which contains 10 mg or one third the amount of PSE as the dosage form. The reference product can also be compared to an extended relief product that was previously approved by the United States Food and Drug Administration that comprises one or more of the actives.

As used herein, the term "treat" or "treating" includes preventing, alleviating, ameliorating, inhibiting, or mitigating one or more health conditions in a mammal, in particular a human, and in one example, an adult human. Non-limiting examples of health conditions can include respiratory conditions.

As used herein, the articles "a" and "an" are understood to mean one or more of the material that is claimed or described, for example, "an immediate release portion" or "a polymer".

All weights, measurements and concentrations herein are measured at 23 degrees Celsius (° C.) and 50% relative humidity, unless otherwise specified.

All percentages, parts and ratios as used herein are by weight of the portion of the dosage form, unless otherwise specified. All such weights as they pertain to listed ingredients are based on the active level and, therefore do not include solvents or by-products that may be included in commercially available materials, unless otherwise specified.

Due to the different duration of action and pharmacokinetic behavior of the actives, it is difficult to formulate an extended release product that has the desired dissolution profile and provides a therapeutic concentration of all of the actives for an extended period of time. In one aspect, an extended period of time can be for at least 6 hours, alternatively for at least 8 hours, alternatively for at least 10 hours, alternatively for at least 12 hours.

In one aspect, the dosage form can maintain a therapeutically effective amount of all actives for at least 12 hours. In one aspect, the dosage form can be adapted to maintain a therapeutically effective amount of a pain reliever, pseudoephedrine, and dextromethorphan for at least eight hours as determined by matching or exceeding the AUC to reference products. In one aspect, the dosage form is substantially bioequivalent to a reference product over a 12 hour period.

In another aspect, the dosage form can be adapted so the Cmax, Cmin, and/or the AUC of DXM, PSE, and NAP in a human subject is substantially equivalent to the Cmax, Cmin, and/or AUC obtained from repeated administration of the immediate release dosage forms for DXM, PSE, and NAP, which have been approved by the U.S. Food and Drug Administration.

For instance, the Cmax, Cmin, and/or AUC of DXM in a human subject is substantially equivalent to the Cmax, Cmin and/or AUC obtained when three doses of a monographed immediate release formulation having one-third the amount of DXM is dosed every 4 hours over a 12 hour period or when two doses of monographed immediate release formulation having half the amount of DXM is dosed every six hours.

Extended release dosage forms generally have a slower rate of appearance of the drug in the plasma and when the active does appear, the Cmax is lower than that typically observed from an immediate release dosage form at identical dosages. Thus, substantially matching the Cmax of an extended release dosage form to an immediate release dosage form can potentially match the onset of efficacy from the immediate release dosage form.

In one aspect, the dosage form can be a tablet with more than one portion that provides extended relief for an 8 or 12 hour period. In one aspect, the tablet can be a matrix bi-layer tablet. Bi-layer tablets can have some advantages over traditional monolayer tablets. For instance, such tablets can avoid chemical incompatibilities of formulation components, in particular incompatible actives, by physical separation. Additionally, bi-layer tablets can allow for controlled delivery of actives with predetermined dissolution profiles by combining portions with various dissolution patterns or by combining extended release or delayed release portions with immediate release portions.

In one aspect, the bi-layer tablet has a first portion that can be an immediate release layer and a second portion that can be an extended release portion. The immediate release portion can comprise a first active and the extended release portion can comprise a second active. In another aspect, the extended release portion can comprise two or more actives. In one aspect, the immediate release portion can comprise NAP and the extended release portion can comprise DXM and PSE.

In another aspect, to improve the Cmax and the speed in which the actives reach a therapeutic level while still maintaining a therapeutic effect for an extended period of time, a portion of the actives from the extended release portion can be present in the immediate release portion of the bi-layer tablet. For instance, the immediate release portion can comprise a pain reliever, such as NAP, and at least one other active, such as DXM and/or PSE.

In order to formulate an MSR dosage form that provides extended relief, the dissolution profile of the active can be modified. One way to modify the dissolution profile is to vary the amount or type of excipient that is used in the dosage form. In one aspect, the excipient can be a polymer and the dissolution profile can be impacted by the specific polymer that is used. For instance, using HPMC with different viscosities or varying the concentration of HPMC can impact the dissolution profile of the active.

In order to make a dosage form that comprises DXM and PSE in the same portion, the excipients can be optimized according to the unique physicochemical attributes of the actives. Two examples, corresponding to Examples 1 and 2 described hereafter, were made. The polymer in each example differed by the viscosity of the polymer. A dissolution profile was created for each example using the Dissolution Method described hereafter.

In order to determine whether the dissolution profile could provide an efficacious level of active for a 12 hour dose, the dissolution profile was compared to success criteria for both DXM and PSE. The best formulation would fall within or be close to the success criteria for both DXM and PSE.

The success criteria was created by determining what the dissolution profile for an ideal 12 hour formula could look like for DXM and PSE, which was determined by comparing the dissolution profiles of one or more commercially available products containing the actives, utilizing compendia guidance and extrapolating the formula for twelve hours, if necessary. The success criteria for DXM are shown in Table 1 and the success criteria for PSE are shown in Table 2 below.

TABLE 1

Success Criteria for DXM

| Time (hour) | Percent of Drug Dissolved |
| --- | --- |
| 1 | 35-65% |
| 3 | 60-90% |
| 8 | >75% |

TABLE 2

Success Criteria for PSE

| Time (hour) | Percent of Drug Dissolved |
| --- | --- |
| 1 | 40-70% |
| 3 | >75% |
| 6 | >85% |

Figure 2:
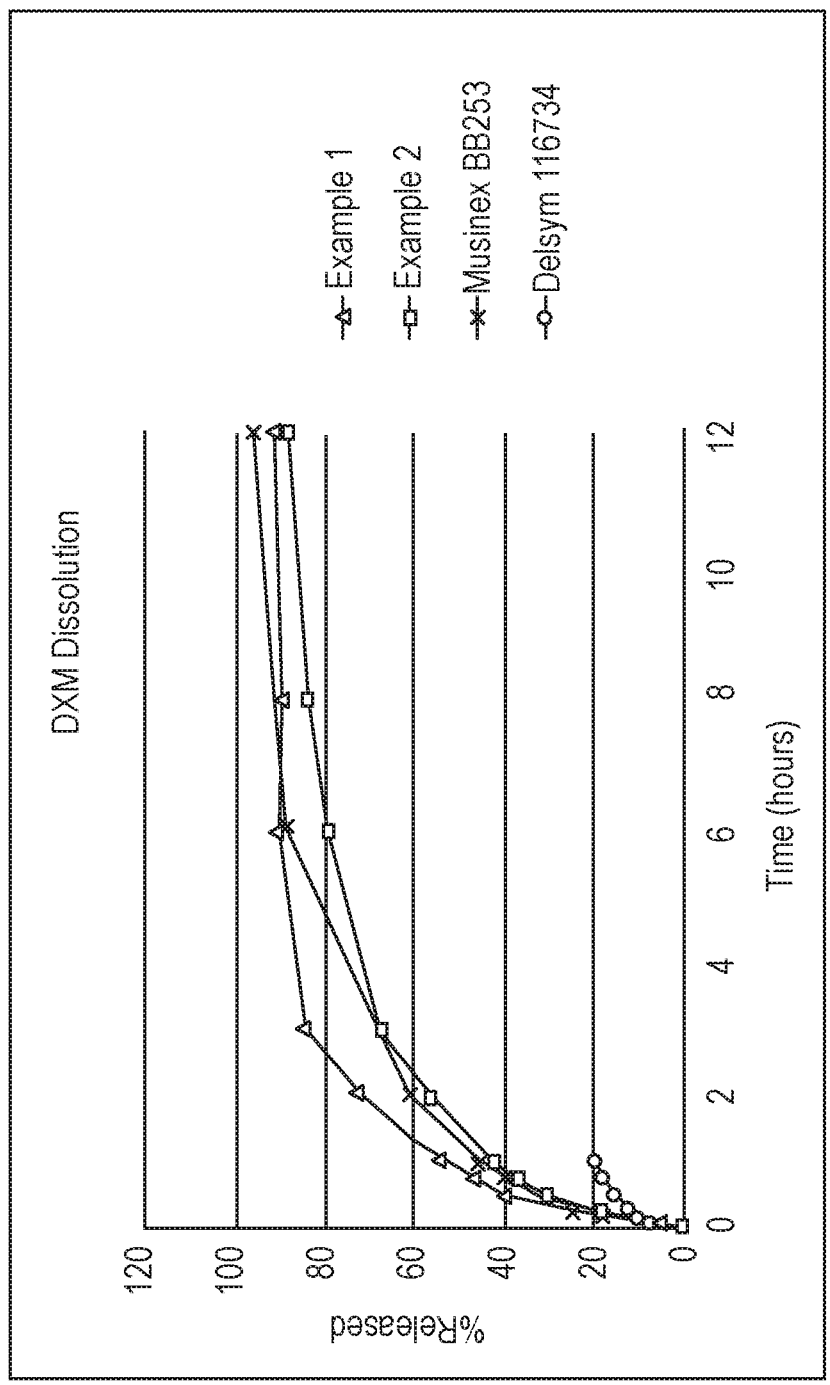
FIG. 2 shows the dissolution profile for dextromethorphan for Examples 1-2 versus two reference products, as determined by the Dissolution Method.

FIG. 2 shows the dissolution profile for DXM for Examples 1-2, described hereafter, and 2 reference products. The reference products are Delsym® (Lot #116734) and Mucinex® DM (Lot #BB253). The dissolution of Delsym® was only measured for 1 hour.

Figure 3:
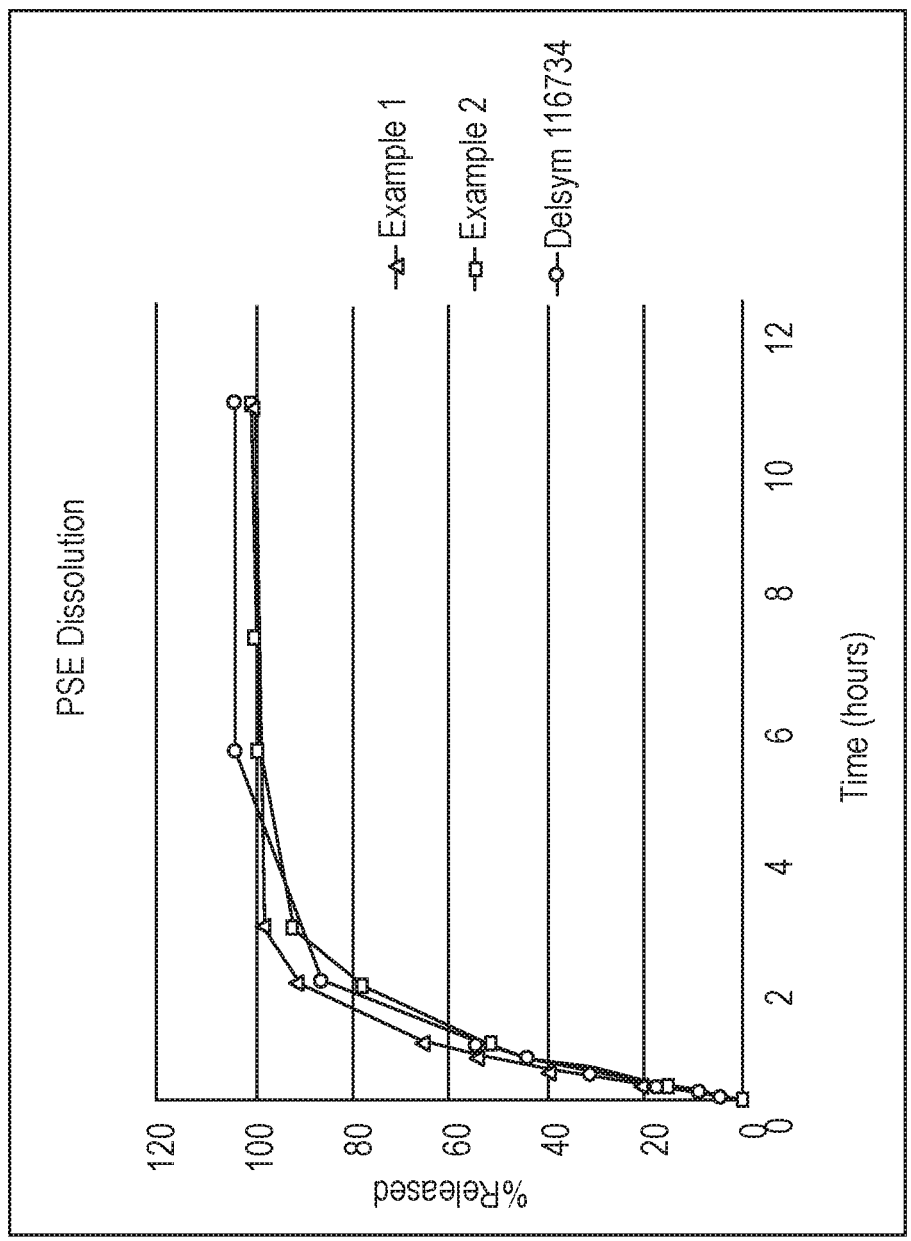
FIG. 3 shows the dissolution profile for pseudoephedrine for Examples 1-2 versus a reference product, as determined by the Dissolution Method.

FIG. 3 shows the dissolution profile for PSE for Examples 1-2, described hereafter, and 1 reference product. The reference product is Aleve-D® (Lot #3AE1326). The dissolution profile for DXM and PSE were determined by the Dissolution Method described hereafter. The dissolution reported for DXM and PSE is an average of three samples for each Example.

Example 1, having 20% by weight of the extended release portion METHOCEL™ K100LV which is an HPMC with a viscosity of 80-120 centipoise (cP), had a faster release of DXM as compared to Example 2. Example 2 comprises 20% by weight of the extended release portion METHOCEL™ K 100M, which is a HPMC with a viscosity of 80,000-120,000 cP. The percent dissolution for both Example 1 and Example 2 fell within the success criteria for DXM and PSE. However, Example 1 had a faster rate of dissolution for DXM and PSE as compared to Example 2. Based on the dissolution models, it is believed that DXM and PSE in Example 1 may be released too quickly and thus may not provide an efficacious level of active throughout the entire period between doses if tested in vivo. Based on the dissolution models, it is believed that Example 2 may provide a therapeutic level of active for the entire dosage interval if tested in vivo.

When compared to the reference products, Example 1 had a faster release of DXM at 2 hours as compared to Mucinex® DM and a similar rate of release of PSE as compared to Aleve-D® at 2 hours. Example 2 had a similar rate of release of DXM and PSE as compared to Mucinex® DM and Aleve-D®, respectively. Delsym® had the slowest rate of release out of the formulas tested, with only 20% DXM released at 1 hour.

Figure 4:
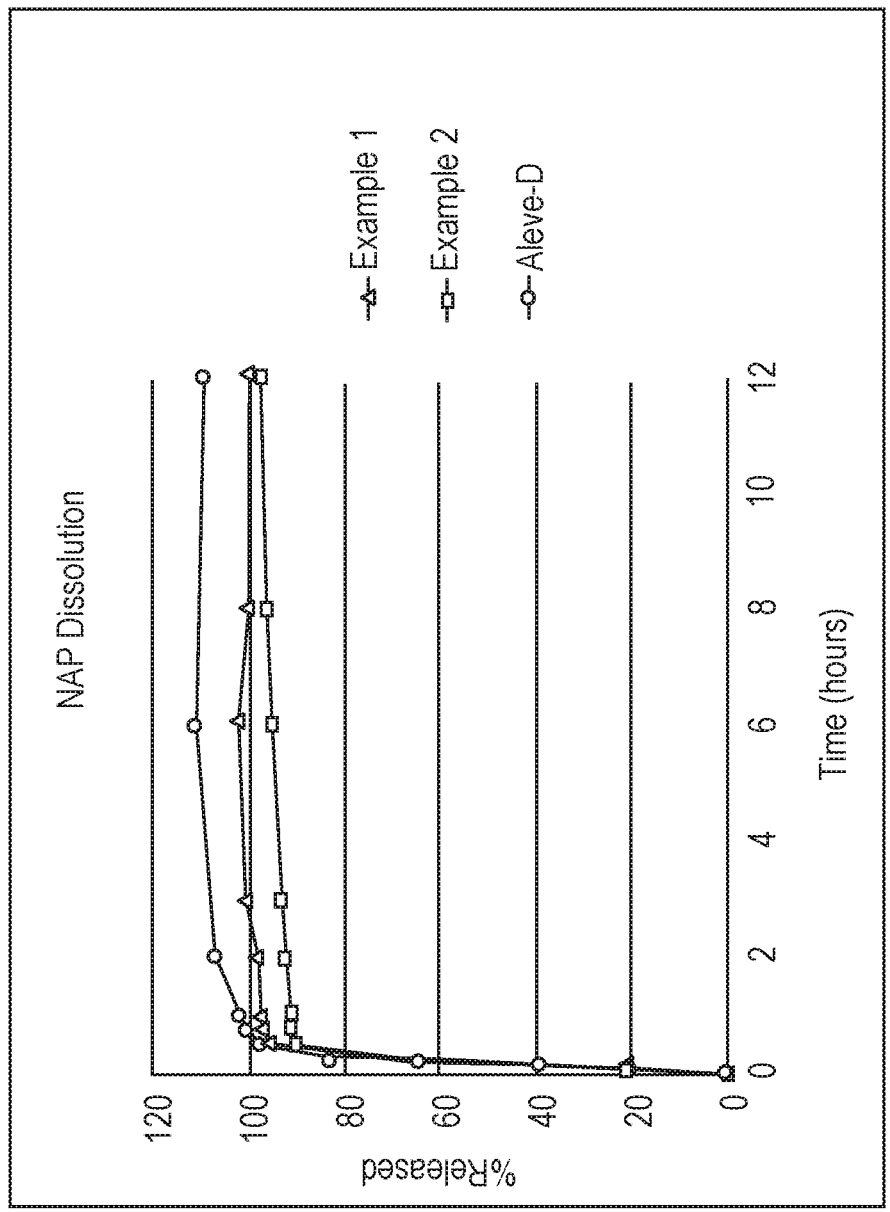
FIG. 4 shows the dissolution profile for naproxen for Examples 1-2 versus a reference product, as determined by the Dissolution Method.

FIG. 4 shows the dissolution profile for NAP for Examples 1-2, described hereafter, and one reference product. The reference product is Aleve-D® (Lot #3K1936). The dissolution profiles were determined by the Dissolution Method described hereafter. The dissolution reported is an average of three samples for each Example.

Examples 1-2 and Aleve-D® had similar dissolution profiles for NAP and all reached over 90% dissolution of NAP within 1 hour. Based on the dissolution models, it is believed that NAP in Example 1 and 2 could provide a therapeutic level of active for the entire dosage interval if tested in vivo. It is believed that the composition of the extended release layer may impact the release profile of the NAP in the immediate release layer. Modifying the excipients in the immediate release layer may increase or decrease the rate NAP is released from the immediate release layer.

In one aspect, the dosage form can be adapted to reach complete dissolution of DXM within about 3 hours, alternatively within about 6 hours, alternatively within about 8 hours, alternatively within about 12 hours. Dissolution can be considered complete when 75% of DXM in the dosage form is dissolved. In one aspect, the dosage form can be adapted to reach complete dissolution of DXM in less than about 4 hours, alternatively in less than about 6 hours. In one aspect, the dosage form can reach greater than about 65% dissolution of DXM within about 3 hours. Dissolution can be measured according to the Dissolution Method described hereafter.

In one aspect, the dosage form is adapted to reach complete dissolution of PSE within about 3 hours, alternatively within about 2 hours, alternatively within about 1 hour. Dissolution can be considered complete when 75% of PSE in the dosage form is dissolved. In one aspect, the dosage form is adapted to reach complete dissolution of PSE in less than about 2 hours. In one aspect, the dosage form can reach greater than about 75% dissolution of PSE within about 2 hours. In one aspect, the dosage form can reach greater than about 80% dissolution of PSE within about 2 hours. In another aspect, the dosage form can reach greater than about 90% dissolution of PSE within about 2 hours. Dissolution can be measured according to the Dissolution Method described hereafter.

In one aspect, the dosage form can be adapted to reach complete dissolution of NAP within about 2 hours, alternatively within about 1 hour, alternatively within about 30 minutes. Dissolution can be considered complete when 80% of NAP in the dosage form is dissolved. In one aspect, the dosage form can be adapted to reach complete dissolution of NAP in less than about 1 hour, alternatively in less than about 30 minutes. In one aspect, the dosage form can reach greater than about 90% dissolution of NAP within about 30 minutes. Dissolution can be measured according to the Dissolution Method described hereafter.

In order to minimize the oxidation of PSE and/or DXM, one or more stabilizing agents may be used. Stabilizing agents can include chelating agents, antioxidants, and combinations thereof. The dosage form can comprise a stabilizing agent in the immediate release layer and/or the extended release layer. In one aspect, the immediate release layer can be substantially free of a stabilizing agent. As used herein, substantially free of stabilizing agent means that the immediate release layer comprises less than about 0.1% stabilizing agent, alternatively less than about 0.01%, alternatively less than about 0.001%, alternatively less than about 0.0001%, all by weight of the immediate release layer.

In one aspect, the stabilizing agent can be a chelating agent. Non-limiting examples of chelating agents suitable for use in the present invention can include ethylenediaminetetraacetic acid (EDTA), citric acid, malic acid, tartaric acid, lactic acid, aspartic acid, glutamic acid, lysine, sodium hexametaphosphate, and combinations thereof. The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes EDTA as well as its salt forms. One advantage to including a chelating agent is that it can bind metal ions, thereby reducing the oxidation of PSE and/or DXM and the production of degradation products.

The amount of chelating agent present in the dosage form will depend on the particular chelating agent selected and the amount of PSE and/or DXM present in the dosage form. In one aspect, the dosage form can contain a safe and effective amount of a chelating agent suitable for achieving the desired chelating effect. In one aspect, the dosage form can contain from about 0.2 mg to about 100 mg of a chelating agent, alternatively from about 0.5 mg to about 60 mg, alternatively from about 1 mg to about 40 mg, alternatively about 2 mg to about 20 mg. In one aspect, the chelating agent can be EDTA and the dosage form can comprise from about 0.5 mg to about 15 mg EDTA, alternatively from about 1 mg to about 10 mg, alternatively from about 3 mg to about 5 mg. In one aspect, the dosage form can comprise from about 0.001% to about 10% chelating agent, alternatively from about 0.01% to about 8%, alternatively from about 0.1% to about 5%, alternatively from about 0.5% to about 3%, all by weight of the dosage form.

In one aspect, the stabilizing agent can be an antioxidant. Non-limiting examples of antioxidants can include ascorbyl palmitate, ascorbic acid, propyl gallate, alpha-tocopherol, butylated hydroxytoluene, butylated hydroxyanisole, bisulfite salts including sodium and potassium bisulfite salts, meta bisulfite salts including sodium and potassium meta bisulfite salts, dithiothreitol, thiourea, sodium thiosulphate, thioglycolic acid, hydroquinone, tert-butyl hydroquinone (TBHQ), acetyl cysteine, and combinations thereof.

The amount of antioxidant present in the dosage form will depend on the particular antioxidant selected and the amount of PSE and/or DXM present in the dosage form. In one aspect, the dosage form can contain from about 0.01 mg to about 5 mg of an antioxidant, alternatively from about 0.05 mg to about 3.5 mg, alternatively from about 0.1 mg to about 2 mg, alternatively from about 0.5 mg to about 1.75 mg. In one aspect, the antioxidant can be propyl gallate. In one aspect, the dosage form can comprise from about 0.001% to about 3% antioxidant, alternatively from about 0.01% to about 1.5%, alternatively from about 0.1% to about 1%, alternatively from about 0.25% to about 0.75%, all by weight of the dosage form. One advantage to including an antioxidant is that it can bind free radicals, thereby reducing the oxidation of PSE and/or DXM and the production of degradation products.

In one aspect, the dosage form can comprise a chelating agent and an antioxidant.

It was found that PSE and/or DXM may be sensitive to pH conditions during processing. In one aspect, the dosage form can comprise a buffering agent for adjusting the pH to minimize the degradation of PSE and/or DXM. In one aspect, the extended release portion can comprise a buffering agent. In one aspect, the immediate release portion does not comprise a buffering agent. In one aspect, the buffering agent can achieve a pH of about 6.0 to about 8.0, in alternatively from about 6.5 to about 7.5, alternatively from about 6.8 to about 7.0. In one aspect, if the pH is less than about 5.5, degradation of PSE and/or DXM may increase. The resulting pH after the dosage form disintegrates and is dissolved into solution can be measured using the pH Test Method described hereafter.

In one aspect, the buffering agent can be basic. The buffering agent can be selected from the group consisting of meglumine, glycine, sodium carbonate, calcium carbonate, sodium bicarbonate, phosphate buffer, magnesium hydroxide, and combinations thereof.

In one aspect, the dosage form can be substantially free of methcathinone. As used herein, substantially free of methcathinone means that the dosage form comprises less than about 0.1%, alternatively less than about 0.05%, alternatively less than about 0.01%, alternatively less than about 0.001% methcathinone, by weight of the dosage form. In one aspect, substantially free of methcathinone can mean the presence of methcathinone is non-detectable according to the Stability Indicating HPLC Method described hereafter.

In one aspect, the dosage form can comprise less than about 0.2% methcathinone, alternatively less than about 0.1%, alternatively less than about 0.01%, alternatively less than about 0.05%, alternatively less than about 0.001%, alternatively less than about 0.0075%, alternatively less than about 0.0005%, alternatively less than about 0.0001%. In one aspect, the dosage form can comprise less than about 80 µg methcathinone, alternatively less than about 60 µg, alternatively less than about 40 µg, alternatively less than about 30 µg, alternatively less than about 20 µg, alternatively less than about 10 µg. The level of methcathinone can be measured according to the Stability Indicating HPLC Method described hereafter.

In one aspect, the dosage form can be substantially free of 10-keto-dextromethorphan. As used herein, substantially free of 10-keto-dextromethorphan means that the dosage form comprises less than about 0.5%, alternatively less than about 0.1%, alternatively less than about 0.05%, alternatively less than about 0.01%, alternatively less than about 0.001%, alternatively less than about 0.0001% 10-keto-dextromethorphan, by weight of the dosage form. In one aspect, substantially free of 10-keto-dextromethorphan can mean the presence of 10-keto-dextromethorphan is non-detectable according to the Stability Indicating HPLC Method described hereafter.

In one aspect, the dosage form comprises less than about 0.2% 10-keto-dextromethorphan, by weight of the dosage form, alternatively less than about 0.1%, alternatively less than about 0.01%, alternatively less than about 0.0075%, alternatively less than about 0.0005%, alternatively less than about 0.0001%. In one aspect, the dosage form can comprise less than about 80 µg 10-keto-dextromethorphan, alternatively less than about 60 µg, alternatively less than about 40 µg, alternatively less than about 30 µg, alternatively less than about 20 µg, alternatively less than about 10 µg. The level of 10-keto-dextromethorphan can be measured according to the Stability Indicating HPLC Method described hereafter.

The dosage form can comprise a polymer. Non-limiting examples of polymers can include hydrophilic polymers, water in-soluble polymers, acrylate copolymers, hypromellose acetate succinate, polyvinyl acetates and derivatives (commercially available as Kollicoat®, from BASF, Tarrytown, N.J.), shellac, polyvinyl alcohol, polyethylene glycol, and combinations thereof.

In one aspect, the polymer can be a hydrophilic polymer. Hydrophilic polymers can swell and dissolve slowly in aqueous acidic media, such as the stomach, thereby slowly releasing the actives in the stomach. However, pH increases when the dosage form reaches the intestines. The hydrophilic polymer can dissolve in a controlled quantity and extended release of the actives is achieved throughout the digestive tract.

Non-limiting examples of hydrophilic polymers can include natural or partially or totally synthetic hydrophilic gums such as acacia, gum tragacanth, locust bean gum, guar gum, or karaya gum, modified cellulosic substances such as ethylcellulose, cellulose acetate phthalate, carboxymethylcellulose (CMC) or a salt of CMC, HPMC, hydroxypropyl cellulose, hydroxypropyl methylcellulose phthalate, hydroxypropyl methylcellulose acetate succinate, hydroxyethyl cellulose, cellulose acetate tetrahydrophthalate, cellulose acetate hexahydrophthalate, hydroxypropyl cellulose acetate succinate; proteinaceous substances such as agar, pectin, carrageen, and alginates; and other hydrophilic polymers such as carboxypolymethylene, gelatin, casein, zein, polysaccharides, modified starch derivatives, and combinations thereof.

In one example, the hydrophilic polymer can be HPMC, commercially available as METHOCEL™ ethers (available from Colorcon®, Harleysville, Pa.). In one example, the desired dissolution profile can be achieved using METHOCEL™ K100LV and/or METHOCEL™ K 100M.

Although the desired dissolution profile of the actives can be achieved using METHOCEL™ K100LV and/or METHOCEL™ K100M, it was found that both forms of HPMC contain iron which can increase the level of PSE and/or DXM degradation observed. It was found that METHOCEL™ K100M contains more iron than METHOCEL™ K100LV. In one aspect, dosage forms comprising METHOCEL™ K100M can have a higher level of PSE and/or DXM degradants.

In one aspect, the dosage form can comprise less than about 5 ppm iron, alternatively less than about 3 ppm, alternatively less than about 2 ppm, alternatively less than about 1 ppm.

In one aspect, the dosage form can comprise a ratio of PSE to polymer of from about 0.10 to about 3.0, alternatively from about 0.50 to about 2.0, alternatively from about 0.75 to about 1.5, all on a weight basis.

In another aspect, the polymer can be a water-insoluble polymer. In one aspect, the water-insoluble polymers do not dissolve in solutions of a pH below 5 and thus do not dissolve in the low pH environment found in the gastric fluids of the stomach. Non-limiting examples of water-insoluble polymers can include polyacrylic acids, acrylic resins, acrylic latex dispersions, polyvinyl acetate phthalate, and other polymers common to those of skill in the art.

Non-limiting examples of acrylate copolymers can include methyl-methacrylate esters copolymerized with methacrylic acid, acrylic acid and esters copolymerized with methacrylic acid and esters, ammonia-containing acrylate copolymers, and combinations thereof.

In one aspect, the polymer can be an anionic copolymer based on methyl acrylate, methyl methacrylate, and methacrylic acid. In one aspect, the polymer can comprise Poly(methyl acrylate-co-methyl methacrylate-co-methacrylic acid) 7:3:1 polymer marketed under the tradename "Eudragit® FS30D", available from Evonik Industries, Darmstadt, Germany. In another aspect, the polymer can further comprise Poly(methacrylic acid-co-ethyl acrylate) 1:1 polymer, marketed under the tradename "Eudragit® L30D", commercially available from Evonik Industries, Darmstadt, Germany.

In one aspect, the polymer can be an extended release polymer. In one aspect, the extended release polymer can be a hydrophilic polymer such as HPMC.

In one aspect, the extended release portion can comprise a polymer. The extended release portion can comprise from about 10% to about 30% polymer, alternatively from about 15% to about 25% polymer, alternatively from about 18% to about 23% polymer, by weight of the portion. In another aspect, the extended release portion can comprise from about 25% to about 60% polymer, alternatively from about 30% to about 50% polymer, alternatively from about 35% to about 45%, alternatively from about 40% to about 50%, by weight of the portion.

In one aspect, the glass transition temperature ($T_g$) of the polymer can be relatively resistant to change upon exposure to water. The polymer can be exposed to water during processing from either tablet components or tableting pressures. An advantage of working with a polymer with a $T_g$ that is relatively resistant to change is that the polymer is relatively rugged to water exposure during processing. Polymers that are mostly amorphous or partly amorphous can have a significant decrease in $T_g$ with increasing water content, which means that additional care must be taken to protect against water exposure during processing or with incoming excipients to ensure that the polymer system does not decrease the $T_g$ range during processing. Should this happen, manufacturing issues, such as hardness of the dosage forms, could be impacted.

The $T_g$ takes place over a temperature range. $T_i$ is the inflection temperature and $T_f$ is the extrapolated onset temperature. The $T_i$ for the polymer at about 75% relative humidity can be greater than about 25° C., alternatively greater than about 40° C., alternatively greater than about 60° C., alternatively greater than about 80° C., alternatively greater than about 90° C., alternatively greater than about 100° C., alternatively greater than about 110° C., alternatively greater than about 115° C., alternatively greater than about 120° C., as determined by the Glass Transition Temperature Test Method described hereafter. In another aspect, the $T_i$ for the polymer at about 75% relative humidity can be from about 40° C. to about 175° C., alternatively from about 60° C. to about 160° C., alternatively from about 90° C. to about 155° C., alternatively from about 100° C. to about 150° C., alternatively from about 110° C. to about 148° C., alternatively from about 120° C. to about 145° C., alternatively from about 122° C. to about 139° C., as determined by the Glass Transition Temperature Test Method described hereafter.

The glass transition temperature can be determined using the following method. First, a 4-5 mg sample of polymer can be transferred into a standard open aluminum sample pan, available from DSC Consumables Inc. (Austin, Minn.). The open pan can equilibrate for several days inside a chamber that is controlled at 75% relative humidity. After the sample is equilibrated, the sample pan can be hermetically sealed and ASTM Method E1356-08 (Apr. 30, 2013) and can be run on a High Sensitivity Differential Scanning Calorimeter, such as the Seiko X-DSC7000 available from Seiko Instruments Inc., per ASTM method E1356-08 over a temperature range of 5° C. to 250° C. The $T_i$ and $T_f$ can be determined as per the ASTM method. In one aspect, the polymer can be a hypromellose and can have a viscosity from about 80 cP to about 250,000 cP, alternatively from about 100 cP to about 150,000 cP, alternatively from about 25,000 cP to about 100,000 cP, alternatively from about 50,000 cP to about 80,000 cP, as measured by 35 United States Pharmacopeia (USP)<911> (official from Dec. 1, 2012) and following the method for hypromellose samples having a viscosity type of greater than 600 mPa·S.

In one aspect, from about 50% to about 90% of the polymer particles can be between 106 μm and 212 μm, alternatively from about 60% to about 80%, alternatively from about 70% to about 80%, alternatively from about 72% to about 77%. In another aspect, greater than 75% of the polymer particles can be smaller than 212 μm, alternatively greater than 85%, alternatively greater than 90%, alternatively greater than 95%, alternatively greater than 97%. The polymer particle size distributions can be determined using 35 USP <786> Particle Size Distribution Estimation by Analytical Sieving (official from Dec. 1, 2012) and by using the mechanical agitation for dry sieving method. The particle size can affect the behavior of the formulation during processing, the compressibility of the formulation, and/or the uniformity of the final product.

In one aspect, the immediate release portion can comprise from about 15% to about 50% of a monosaccharide and/or a disaccharide by weight of the immediate release portion, alternatively from about 25% to about 40%, alternatively from about 30% to about 38%. In another aspect, the immediate release portion can comprise greater than about 20% of a soluble excipient, alternatively greater than about 25% by weight of the immediate release layer, alternatively greater than about 30%, alternatively greater than about 33%. In another aspect, the immediate release portion can comprise less than about 50% of a swellable excipient, which includes swellable polymers, by weight of the immediate release portion, alternatively less than about 40%, alternatively less than about 25%, alternatively less than about 20%, alternatively less than about 16%.

The dosage forms can comprise additional excipients, including, but not limited to: lubricants such as microcrystalline cellulose, magnesium stearate, calcium stearate, zinc stearate, powdered stearic acid, hydrogenated vegetable oils, polyethylene glycol, and mineral oil; colorants; binders such as sucrose, lactose, starch paste, povidone and corn syrup; glidants such as colloidal silicon dioxide and talc; surface active agents such as sodium lauryl sulfate, dioctyl sodium sulfosuccinate, tricthanolamine, polyoxyetiylene sorbitan, poloxalkol, and quarternary ammonium salts; preservatives and stabilizers; sweeteners such as lactose, mannitol, glucose, fructose, xylose, galactose, maltose, xylitol, and sorbitol; xanthan gum; and alginic acid.

The dosage form can comprise one or more actives, in particular actives that can help relieve symptoms of a cold, flu, or allergies. Non-limiting examples of actives can include decongestants, expectorants, antihistamines, antitussives, pain relievers, and combinations thereof.

The dosage form can comprise a decongestant. Non-limiting examples of decongestants can include pseudoephedrine, PSE, phenylephrine, and any acceptable salts thereof, and combinations thereof. Non-limiting examples of phenylephrine or salts thereof can include phenylephrine hydrochloride, phenylephrine bitartrate, phenylephrine tannate, and combinations thereof. In one aspect, the dosage form can comprise phenylephrine hydrochloride (PE).

Non-limiting examples of expectorants can include guaifenesin, ambroxol, bromhexine, and any acceptable salts thereof, and combinations thereof. In one aspect, the dosage form does not comprise guaifenesin.

Non-limiting examples of antihistamines can include chlorpheniramine, desloratadine, levocetirizine, diphenhydramine, doxylamine, triprolidine, clemastine, pheniramine, brompheniramine, dexbrompheniramine, loratadine, cetirizine, fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenalidine, picumast, tolpropamine, ramatroban, repirinast, suplatast tosylate aminoalkyl ethers, tazanolast, bromodiphenhydramine, tranilast, carbinoxamine, traxanox, chlorphenoxamine, diphenylpyraline, embramine, p-methyl diphenhydramine, moxastine, orphenadrine, phenyltoloxamine, setastine, ethylenediamine derivatives, chloropyramine, chlorothene, methapyrilene, pyrilamine, talastine, thenyldiamine, thonzylamine hydrochloride, tripelennamine, piperazine, chlorcyclizine, clocinizine, homochlorcyclizine, hydroxyzine, mequitazine, promethazine, thiazinamium metilsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydrolin, mizolastine, phenindamine, terfenadine, tritoqualine, and any acceptable salts thereof, and combinations thereof.

Non-limiting examples of antitussives can include dextromethorphan, DXM, menthol, codeine, chlophedianol, levodropropizine, and any acceptable salt thereof, and combinations thereof.

Non-limiting examples of pain relievers can include acetaminophen, ibuprofen, ketoprofen, diclofenac, NAP, naproxen, aspirin, and any acceptable salt thereof, and combinations thereof.

In one aspect, the dosage form can comprise from about 150 mg to about 300 mg naproxen or a pharmaceutically acceptable salt thereof, such as NAP, alternatively from about 180 mg to about 260 mg, alternatively from about 195 mg to about 225 mg. In one aspect, the dosage form can comprise about 220 mg naproxen or a pharmaceutically acceptable salt thereof. In one aspect, the dosage form can comprise from about 100 mg to about 200 mg naproxen or a pharmaceutically acceptable salt thereof, alternatively 110 mg to about 150 mg.

In another aspect, the dosage form can comprise from about 30 mg to about 80 mg DXM or dextromethorphan, alternatively from about 40 mg to about 70 mg, alternatively from about 55 mg to about 65 mg. In another aspect, the dosage form can comprise more than about 30 mg DXM or dextromethorphan, alternatively more than about 35 mg, alternatively more than about 40 mg, alternatively more than about 50 mg. In one aspect, the dosage form can comprise about 60 mg DXM or dextromethorphan. In one aspect, the dosage form can comprise from 5 mg to 30 mg DXM or dextromethorphan, alternatively 8 mg to 15 mg.

In one aspect, the dosage form can comprise from about 75 mg to about 175 mg PSE or pseudoephedrine, alternatively from about 100 mg to about 150 mg, alternatively from about 110 mg to about 130 mg. In another aspect, the dosage form can comprise about 120 mg PSE or pseudoephedrine.

In one aspect, the dosage form can comprise from about 5 mg to about 15 mg of PE. In one aspect, the dosage form can comprise from about 200 mg to about 600 mg of guaifenesin. In one aspect, the can comprise about 12 mg of chlorpheniramine. In one aspect, the dosage form can comprise about 12.5 to about 25 mg chlophedianol. In one aspect, the dosage form can comprise about 325 mg to about 650 mg acetaminophen, alternatively the dosage form can comprise about 200 mg ibuprofen. In one aspect, the dosage form can further comprise a stimulant such as caffeine.

In one aspect, the dosage form can comprise one or more actives, alternatively two or more actives, alternatively three or more actives, alternatively four or more actives. In one aspect, the dosage form can comprise exactly two actives, alternatively exactly three actives, alternatively exactly four actives. In one aspect, the dosage form can comprise NAP, DXM and PSE. In another aspect, the dosage form can comprise NAP, DXM and PE. In another aspect, the dosage form can comprise NAP and DXM.

Although, a matrix bi-layer can be a preferred dosage form, other dosage forms can be used to obtain the desired dissolution profile. In one aspect, the dosage form can be a tri-layer tablet. One portion can be an immediate release portion and the other portions can be extended release or delayed release portions. The tri-layer tablet can separate incompatible actives and each portion of the tri-layer tablet can have a different active.

In another aspect, the dosage form can be a single layer matrix tablet. The matrix tablet can comprise more than one active. The matrix tablet can comprise a pain reliever, a decongestant, and an antitussive. In one aspect, the pain reliever can be an immediate release component in the matrix tablet and the decongestant and the antitussive can be extended release components that are released from the matrix over an 8 to 12 hour period.

In another aspect, the dosage form can be a capsule comprising at least two populations of particles, where each population of particles comprises an active. The term particle is not meant to be limiting and includes microcrystals, micro-particles, beads, microbeads, powders, granules, pellets, micropellets, nonpareil seeds, and microcapsules. The individual particle populations can be matrix forms, active coated cores, modified release coated cores containing an active, or pure drug actives and their pharmaceutical salts in particle or crystal form. The particles can be mixed in the capsule and designed to provide relief in a human subject for 8 to 12 hours. In one aspect, the particles can be from 200 μm to 1000 μm in its longest dimension, alternatively from 300 μm to 900 μm, alternatively from 400 μm to 800 μm, alternatively from 500 μm to 725 μm.

In one aspect, the dosage form can be consumed by swallowing it whole. The dosage form can be a size that is easy to swallow. In one aspect, a dose of medication can be in one or more dosage forms that weigh less than about 1.5 g, alternatively less than about 1.25 g, alternatively less than about 1 g, alternatively less than about 900 mg, alternatively less than about 875 mg, alternatively less than about 850 mg. In one aspect, a dose of medication can be in one or more dosage forms that weigh from about 700 mg to about 1.25 g, alternatively from about 750 mg to about 1 g, alternatively from about 800 mg to about 900 mg, alternatively from about 820 mg to about 860 mg. In another aspect, the dosage form can be a chewable tablet.

In one aspect, the immediate release portion can weigh between about 350 mg and about 500 mg, alternatively between about 400 mg and about 470 mg, alternatively between about 425 mg and about 450 mg. In another aspect, the extended release portion can weigh between about 325 mg and about 475 mg, alternatively between about 360 mg and about 430 mg, alternatively between about 390 mg and about 410 mg. In another aspect, the weight ratio of the immediate release portion to the extended release portion can be greater than about 1:3, alternatively greater than about 1:2, alternatively greater than about 1:1. In another aspect, the weight ratio of immediate release portion to extended release portion can be from about 1:2 to about 2:1, alternatively from about 7:10 to about 7:4, alternatively from about 17:10 to about 7:4, alternatively from about 17:20 to about 3:2, alternatively from about 9:10 to about 13:10, alternatively from about 19:20 to about 23:20, alternatively from about 1:1 to about 11:10.

Method of Improving the Stability of a MSR Dosage Form

The present invention also relates to a process for improving the stability of a MSR dosage form comprising pseudoephedrine, or a pharmaceutically acceptable salt thereof.

In one aspect, a method of improving the stability of a dosage form can comprise the steps of:
  a. granulating a first mixture comprising a pain reliever to form a plurality of first portion granules;
  b. spraying the plurality of first portion granules with a binding solution;
  c. drying the plurality of first portion granules to 40° C.;
  d. optionally passing the dried plurality of first portion granules through a mesh screen;
  e. blending the plurality of first portion granules with a first portion excipient to form an immediate release mixture;

f. blending a second mixture comprising pseudoephedrine, or a pharmaceutically acceptable salt thereof, and an extended release polymer;

g. optionally adding a stabilizing agent and mixing to form a plurality of second portion granules;

h. optionally drying the plurality of second portion granules;

i. blending the second portion granules with a second portion excipient to form an extended release mixture; wherein the extended release mixture comprises less than about 0.01% methcathinone;

j. forming a dosage form comprising a first layer of the immediate release mixture and a second layer of the extended release mixture.

In one aspect, the first mixture is wet granulated such as in a fluid bed granulator or a high shear wet granulator. Alternatively, the first mixture is dry granulated such as by roller compaction.

In one aspect, the first mixture can comprise a pain reliever selected from the group consisting of acetaminophen, ibuprofen, ketoprofen, diclofenac, naproxen, aspirin, pharmaceutically acceptable salts thereof, and combinations thereof. In one aspect, the first mixture can further comprise an antitussive such as DXM.

In one aspect, the first mixture can comprise at least one polymer. In another aspect, the first mixture can comprise sucrose.

In one aspect, the binding solution can be water. In another aspect, the binding solution can comprise excipients such as starch, pre-gelatinized starch, starch paste, povidone, sucrose, polyethylene glycol and/or polymers such as tragacanth, HPMC, ethylcellulose, hydroxypropyl cellulose, carboxymethyl cellulose, acacia, gelatin, cellulose, polymethacrylates, polyvinyl alcohols, polyvinyl pyrrolidone, and combinations thereof. One advantage to including an excipient in the binding solution is that it can help to bind the materials together to form particle agglomerates.

In one aspect, the second mixture can comprise an antitussive such as DXM.

In one aspect, the stabilizing agent can be added to the second mixture with the pseudoephedrine and extended release polymer before blending, in another aspect the stabilizing agent can be added during blending, and in yet another aspect the stabilizing agent can be added after blending. In one aspect, the stabilizing agent can include EDTA and/or propyl gallate. In one aspect, the granulation fluid can comprise water. In one aspect, the stabilizing agent can be dissolved in the granulation fluid before it is sprayed on the second mixture. One advantage to including a stabilizing agent to the granulation fluid is that it can help reduce the formation of methcathinone and/or 10-keto-dextromethorphan. In one aspect, the granulation fluid can also comprise a buffering agent. In one aspect, the granulation fluid is atomized before it is added to the second mixture. One advantage to atomizing the fluid is that it can create small droplets of granulation fluid which can help to reduce the gelling of HPMC, which can help with processing.

In one aspect, the second mixture can be granulated by a wet granulation or a dry granulation process. In another aspect, the second mixture can be made by dry blending the pseudoephedrine, or a pharmaceutically acceptable salt thereof. In one aspect, the second mixture can be substantially free of water. It was found that water can enable the oxidation reaction of PSE and/or DXM and can increase the formation of methcathinone and/or 10-keto-dextromethorphan degradants. However, it was found that the addition of the stabilizing agent, even in the presence of water, can capture the catalysts and/or free radicals and can reduce the formation of degradants.

In one aspect, the second portion granules can be dried to about 40° C. to about 45° C. in a fluid bed dryer for about 90 minutes. In one aspect, the second portion granules can be dried at room temperature in a fluid bed dryer for about 4 hours. It was found that the application of heat using an air flow heat source, such as a fluid bed dryer, can increase the degradation of PSE and/or DEX. One advantage to drying the second portion granules at room temperature is that it can reduce the formation of methcathinone and/or 10-keto-dextromethorphan.

In one aspect, the plurality of second portion granules can optionally be placed in a wet mill to reduce particle size before they are dried. In one example, the dried second portion granules can optionally be dry milled to break up clumps that may have formed during processing.

In one aspect, the method can be conducted (i) in the absence of water, (ii) in the presence of a stabilizing agent, or both (i) and (ii). In one aspect, in the absence of water means substantially free of water. In one aspect, the method can be conducted in the absence of heat. In one aspect, in the absence of heat means at a temperature below about 45° C.

Degradation Test

In order to determine the cause of the PSE and/or DXM degradation, the Degradation Test was performed. The Degradation Test included three parts: Part 1 tested the effect of excipients on degradation; Part 2 tested the effect of catalysts; and Part 3 tested the effect of processing steps and a chelating agent on degradation.

Part 1: Excipients

Different HPMC excipients known to contain iron were tested to assess the effect on PSE and/or DXM degradation. The test was performed according to the Degradation Assay Part 1 described hereafter.

Part 1 of the Degradation Test showed that when static heat was used to dry the samples, neither methcathinone nor 10-keto-dextromethorphan was detectable according to the Stability Indicating HPLC Method described hereafter.

Part 2: Catalysts

Catalysts (iron (Iron III) Chloride) and hydrogen peroxide) were tested to assess the effect on PSE and/or DXM degradation. The test was performed according to the Degradation Assay Part 2 described hereafter.

Table 3 summarizes the results from this test. Methcathinone is reported as the peak area of methcathinone divided by the peak area of parent PSE in the sample. 10-Keto-Dextromethorphan is reported as the peak area of 10-Keto-Dextromethorphan divided by the peak area of parent DEX in the sample.

TABLE 3

| Mixture | % of PSE Peak (Methcathinone) | % of DEX Peak (10-Keto-Dextromethorphan) |
|---|---|---|
| PSE + Deionized Water | Non-detectable | N/A |
| PSE + 10 ppm $Fe^{3+}$ (Aqueous Solution) | 0.8 | N/A |
| PSE + 10 ppm $Fe^{3+}$ (Aqueous Solution) + 3% $H_2O_2$ (Aqueous Solution) | 24.7 | N/A |
| PSE + DXM + Deionized Water | Non-detectable | Non-detectable |
| PSE + DXM + 10 ppm $Fe^{3+}$ (Aqueous Solution) | Non-detectable | Non-detectable |
| PSE + DXM + 10 ppm $Fe^{3+}$ (Aqueous Solution) + 3% $H_2O_2$ (Aqueous Solution) | 7.0 | 4.0 |
| PSE + DXM + METHOCEL™ K100M[1] + Deionized Water | 1.5 | 0.8 |

TABLE 3-continued

| Mixture | % of PSE Peak (Methcathinone) | % of DEX Peak (10-Keto-Dextromethorphan) |
|---|---|---|
| PSE + DXM + 10 ppm $Fe^{3+}$ (Aqueous Solution) + METHOCEL ™ K100M[1] | 6.3 | 4.4 |
| PSE + DXM + 10 ppm $Fe^{3+}$ (Aqueous Solution) + 3% $H_2O_2$ (Aqueous Solution) + METHOCEL ™ K100M[1] | 13.2 | 3.5 |

[1]Available from Colorcon ® (Harleysville, PA)

Part 2 of the Degradation Test showed that methcathinone was formed when PSE was exposed to iron, and the reaction increased significantly in the presence of iron and hydrogen peroxide. In addition, it was found that both methcathinone and 10-keto-dextromethorphan was formed in the presence of deionized water when METHOCEL™ K100M was present and an air flow heat source was applied in a manner that mimicked the fluid bed dryer processing step.

Part 3: Processing Steps and Chelating Agent

Processing steps and a chelating agent were tested to assess the effect on PSE and/or DXM degradation. The test was performed according to the Degradation Assay Part 3 described hereafter.

Table 4 summarizes the results from this test. Methcathinone is reported as the peak area of methcathinone divided by the peak area of parent PSE in the sample. 10-Keto-Dextromethorphan is reported as the peak area of 10-Keto-Dextromethorphan divided by the peak area of parent DEX in the sample.

slightly more degradation product as compared to METHOCEL™ K100LV. Drying the samples using an air flow heat source to mimic the application of heat during the fluid bed dryer processing step increased the formation of both degradants. Finally, it was also found that the presence of EDTA reduced the formation of both degradants.

Degradation Assay

Part 1:

Mixtures of actives (PSE and DXM) and two grades of HPMC (METHOCEL™ K100M and METHOCEL™ K100LV) were prepared at the ratios described in Table 5. Approximately 2-5 g were prepared for each sample. The samples were mixed using a mortar and pestle for 5 to 6 minutes.

Wet and dry preparations of the samples were prepared, with 20% (wt/wt) deionized water added to an aliquot of the dry mixture for the wet preparation. After the mixtures were prepared, the samples were divided into two portions and one portion of each sample was placed in a 50° C. isotemp oven to dry for 5 days and the other portion was placed in a 70° C. isotemp oven to dry for 5 days.

An aliquot of each sample was taken to give a final sample concentration of 0.5-1.0 mg/mL for analysis. Samples were analyzed using the Stability Indicating HPLC Method described hereafter.

Part 2:

Mixtures of actives (PSE and DXM) and HPMC (METHOCEL™ K100M) were prepared at the ratios described in Table 5. Approximately 2-5 g were prepared for

TABLE 4

| | Processing Condition of Sample Tested | Replicate | % of PSE Peak (Methcathinone) | % of DEX Peak (10-Keto-Dextromethorphan) |
|---|---|---|---|---|
| PSE + DXM + METHOCEL ™ K100M[1] | Dry Mixture | 1 | Non-detectable | Non-detectable |
|  |  | 2 | Non-detectable | Non-detectable |
| PSE + DXM + METHOCEL ™ K100M[1] + Deionized water | Wet Mixture Before Drying | 1 | 0.09 | 0.08 |
|  |  | 2 | 0.04 | 0.05 |
| PSE + DXM + METHOCEL ™ K100LV[2] + Deionized water | Wet Mixture Before Drying | 1 | 0.03 | 0.02 |
|  |  | 2 | Non-detectable | Non-detectable |
| PSE + DXM + METHOCEL ™ K100M[1] + Deionized water | Dried in 50° C. Convection Oven (2 hr) | 1 | 0.3 | 0.2 |
|  |  | 2 | 0.2 | 0.2 |
| PSE + DXM + METHOCEL ™ K100LV[2] + Deionized water | Dried in 50° C. Convection Oven (2 hr) | 1 | 0.2 | 0.3 |
|  |  | 2 | 0.1 | 0.1 |
| PSE + DXM + METHOCEL ™ K100M[1] + Deionized water | Dried with hair dryer (15 min) | 1 | 1.6 | 0.6 |
|  |  | 2 | 1.1 | 0.3 |
| PSE + DXM + METHOCEL ™ K100LV[2] + Deionized water | Dried with hair dryer (15 min) | 1 | 1.1 | 0.4 |
|  |  | 2 | 0.6 | 0.5 |
| PSE + DXM + METHOCEL ™ K100M[1] + Deionized water + EDTA | Dried with hair dryer (15 min) | 1 | 0.04 | 0.03 |
|  |  | 2 | 0.06 | 0.07 |
| PSE + DXM + METHOCEL ™ K100LV[2] + Deionized water + EDTA | Dried with hair dryer (15 min) | 1 | Non-detectable | Non-detectable |
|  |  | 2 | Non-detectable | Non-detectable |

[1,2]Available from Colorcon ® (Harleysville, PA)

Part 3 of the Degradation Test showed that both methcathinone and 10-keto-dextromethorphan were formed with only deionized water in the presence of METHOCEL™ K100M and METHOCEL™ K100LV. However, it was found that samples with METHOCEL™ K100M produced each sample. The samples were mixed using a mortar and pestle for 5 to 6 minutes.

Some samples, as noted in Table 3, were spiked with a 10 ppm iron and/or 3% hydrogen peroxide aqueous solution. 20% (wt/wt) deionized water was added drop-by-drop until a paste was formed. Samples were then dried using an 1875 watt hair dryer (available from Conair Corp., East Windsor, N.J.) for 15 minutes.

An aliquot of each sample was taken to give a final sample concentration of 0.5-1.0 mg/mL for analysis. Samples were analyzed using the Stability Indicating HPLC Method described hereafter.

Part 3:

Mixtures of actives (PSE and DXM) and two grades of HPMC (METHOCEL™ K100M and METHOCEL™ K100LV) were prepared at the ratios described in Table 5. Approximately 2-5 g were prepared for each sample. The samples were mixed using a high speed blender on pulse setting for 5 to 6 minutes. A spatula was used to scrape the sides of the blender.

Some samples, as noted in Table 4, were prepared with 20% (wt/wt) deionized water and/or 1% (w/v) EDTA solution. The samples were then dried in a 50° C. convection oven or using an 1875 watt hair dryer (available from Conair Corp., East Windsor, N.J.) for 15 minutes.

An aliquot of each sample was taken to give a final sample concentration of 0.5-1.0 mg/mL for analysis. Samples were analyzed using the Stability Indicating HPLC Method described hereafter.

TABLE 5

| | | | Wt. % Ratios | |
|---|---|---|---|---|
| Sample | PSE | DXM | METHOCEL ™ K100M | METHOCEL ™ K100LV |
| 1 | 3 | 1 | 0 | 0 |
| 2 | 1 | 0 | 1 | 0 |
| 3 | 1 | 0 | 0 | 1 |
| 4 | 0 | 1 | 1 | 0 |
| 5 | 0 | 1 | 0 | 1 |
| 6 | 3 | 1 | 2 | 0 |
| 7 | 3 | 1 | 0 | 2 |

Stability Indicating HPLC Method

This method is applicable for the determination of methcathinone and 10-keto-dextromethorphan in sample aliquots from the Degradation Assay.

Samples were assayed by High Performance Liquid Chromatography (HPLC) using the Agilent 1260 Infinity Series HPLC system with 1260 Infinity Quaternary Pump (G1311B) and Infinity 1260 Diode Array Detection (G1315D), all commercially available from Agilent Technologies, Santa Clara, Calif. The HPLC column was a Waters Atlantis T3 column, 3 µm, 4.6×100 mm (available from Waters Corp., Milford, Mass.).

First, the stock and working standard solutions were prepared fresh at the time of use.

Standard Solution Preparation

Keto-DEX Stock Solution 10 mg±0.0001 of the 10-keto-dextromethorphan Reference Standard was weighed into a 100 mL volumetric flask and diluted to volume with methanol. The solution was then mixed until all solids dissolved.

PSE Related Substance Solution 1 mL vial of the methcathinone standard (1.0 mg/mL in 1 mL of methanol) was diluted to 100 mL with methanol. This yielded a stock solution of 0.01 mg/mL methcathinone.

Working Standard Solution 48 mg of PSE and 24 mg DXM was transferred to a single 100 mL volumetric flask. 5 mL of Keto-DEX Stock Solution and 5 mL of PSE Related Substance Solution were pipetted into the flask. 50 mL methanol was added to the flask and brought to volume with water. The flask required additional water volume to be added after mixing and cooling if the methanol and water solutions outgassed and warmed.

Mobile Phase Preparation

The mobile phases were prepared as follows.

Mobile Phase A: 5 g of HPLC grade Ammonium Acetate was weighed into a 1 L volumetric flask and brought to volume with deionized water. The solution was mixed thoroughly until all solids dissolved. The solution was transferred to a 1 L mobile phase bottle for use. A stir bar was added and the solution was mixed.

Mobile Phase B: 1000 mL of acetonitrile were added to a 1 L mobile phase bottle and allowed to equilibrate to room temperature before use.

Single Granulation Sample Preparation

First, approximately 440 mg of granulation was placed into a 200 mL volumetric flask and brought to volume with methanol. A stir bar was added and the solution was mixed for approximately 120 minutes, or until all large pieces were dissolved. Then, approximately 40 mL of the sample was centrifuged for 10 minutes at 3500 rpm. Approximately 1.5 ml of the sample was aliquoted into the auto sampler vial for analysis.

After the HPLC equipment was calibrated according to the manufacturers' instructions, the following conditions were used:

TABLE 6

| Gradient Conditions | Time (min) | % A | % B |
|---|---|---|---|
| | 0.0 | 88 | 12 |
| | 0.5 | 88 | 12 |
| | 5 | 25 | 75 |
| | 5.5 | 5 | 95 |
| | 6 | 5 | 95 |
| | 6.1 | 88 | 12 |
| | 8 | 88 | 12 |
| Run Time (minutes) | 8 | | |
| Column Temperature (° C.) | 45 | | |
| Flow Rate (mL/min) | 2.0 | | |
| Detector Wavelength (nm) | 262 | | |
| Injection volume (µL) | 5 | | | pH Test Method

First, a Thermo Scientific Orion 320 pH meter (available from Thermo Scientific, Cambridge, Mass.) was calibrated. This is done by turning on the pH meter and waiting for 30 seconds. The electrode was taken out of the storage solution, rinsed with distilled water, and carefully wiped with a scientific cleaning wipe, such as a Kimwipe®. The electrode was submersed in the pH 7 buffer and the calibrate button was pushed. Once the pH icon stopped flashing, the calibrate button was pushed a second time. The electrode was rinsed with distilled water and carefully wiped with a scientific cleaning wipe. The electrode was then submersed into the pH 4 buffer. When the pH icon stopped flashing, the measure button was pushed. The electrode was rinsed with distilled water and carefully wiped with a scientific cleaning wipe. The calibrated pH meter was then used to test the pH of a solution.

Approximately 400 mg of a test dosage form was placed into 10 mL of distilled water. The tablet was not crushed and the water was 23° C. The solution was not stirred at any time. The pH was measured at 5 minutes.

Dissolution Method

The dissolution profiles for dextromethorphan, pseudoephedrine, and naproxen were determined according to the following method. Samples were assayed by HPLC using a USP <711> (Official Feb. 1, 2012) Type I (baskets) dissolution apparatus and a Raptor™ ARC-18 column, 2.7 µm, 150×4.6 mm (available from Restek®, Bellefonte, Pa.).

First, the stock and working standard solutions, described below, were prepared. These solutions were prepared fresh at the time of use.

Standard Solution Preparation

Stock Solution (NAP: 2.44 mg/mL; DXM: 0.660 mg/mL; PSE: 1.32 mg/mL) Into a 50 mL volumetric flask, 122 mg±2 mg of NAP, 33 mg±2 mg of DXM, and 66 mg±2 mg of PSE were weighed. Approximately 20 mL of Methanol were added and the flask was swirled until the contents were fully dissolved. Then the flask was filled to the mark with Methanol.

Working Standard Solution (NAP: 0.244 mg/mL; DXM: 0.066 mg/mL; PSE: 0.132 mg/mL)

Into a 100 mL volumetric flask, 10 mL of stock solution were added by volumetric pipette. The flask was then filled to the line with distilled water.

Sample Preparation

1. All paddle heights were verified to be a distance of 25±2 mm above the bottom of the vessels.

2. The basket speed was programmed to operate at 50 RPM and to maintain a constant temperature of 37.0±0.5° C. throughout the entire test.

3. 900 mL of degassed distilled water ("dissolution media") was transferred into each dissolution vessel.

4. The dissolution media in the dissolution vessels were allowed to equilibrate to temperature (37.0±0.5° C.). The starting in-vessel media temperatures were verified as within this range and documented.

5. 1 tablet was placed into each basket and the RPM was turned to 50. Dissolution testing was commenced by lowering the baskets into the dissolution media and the timer was started. At 15, 30, 45 min, 1, 2, 3, 6, 8 and 12 hours, exactly 1.2 mL of sample from each dissolution vessel was withdrawn using the automated dissolution sampler or manually by using a syringe with an attached cannula and filter to remove the sample volume. Samples were filtered using a Acrodisc® 25 mm Syringe Filter with 5 µm Versapor® membrane.

Manual methods required an increase in pull volume, however, calculations correct for pull volume without media replacement. Once the samples were withdrawn, the filter was removed and each filtered solution was collected into separate vials.

6. The ending in-vessel medium temperatures were verified as still within range (37.0±0.5° C.) shortly after the last sample pull and the temperatures were documented.

After the HPLC equipment was calibrated according to the manufacturers' instructions, the following conditions are used:

TABLE 7

| Gradient Conditions | Time (min) | % A | % B |
|---|---|---|---|
| | 0.0 | 85 | 15 |
| | 4.0 | 40 | 60 |
| | 5.0 | 40 | 60 |
| | 5.1 | 85 | 15 |
| | 8 | 85 | 15 |

TABLE 7-continued

| Gradient Conditions | Time (min) | % A | % B |
|---|---|---|---|
| Mobile Phases | A: 0.1% Trifluoroacetic acid in water | | |
| | B: Acetonitrile | | |
| Run Time (minutes) | 8 | | |
| Column Temperature (° C.) | 50 | | |
| Sample compartment temperature | Ambient | | |
| Flow Rate (mL/min) | 21.5 | | |
| Detector Wavelength (nm) | 262 nm, switch at 5 min to 340 nm | | |
| Injection volume (µL) | 25 | | |

Examples

TABLE 8

Immediate Release Portion A

| | Component | Weight (mg/dose) | % w/w |
|---|---|---|---|
| Granulation | NAP | 220.00 | 50.00 |
| | DXM | 15.00 | 3.41 |
| | Avicel ® PH 102[3] | 136.80 | 31.09 |
| | Starch 1500 ®[4] | 8.80 | 2.00 |
| | Croscarmellose Sodium[5] | 11.00 | 2.50 |
| Extragranular | Starch 1500 ®[4] | 26.40 | 6.00 |
| | Croscarmellose Sodium[5] | 11.00 | 2.50 |
| | Magnesium Stearate | 2.20 | 0.50 |
| Binder spray | Starch 1500 ®[4] (paste) | 8.80 | 2.00 |

[3]Available from FMC BioPolymer (Philadelphia, Pennsylvania)
[4]Available from Colorcon ® (Harleysville, Pennsylvania)
[5]Available from DFE Pharma (Princeton, New Jersey)

A 2000 g batch of Immediate Release Portion A was be made as follows. First the granular materials were fluidized in a Glatt® GPCG 3 fluid bed granulator (available from Glatt Integrated Process Solutions, Binzen, Germany). Then 1000 g of starch paste was added via top spray to form a wet granulate. The granulate was then dried within the fluid bed granulator until the temperature reached 40° C. The dried granulate was passed through a #20 mesh screen. Then, the croscarmellose sodium, magnesium stearate, and the dried granulate were combined and blended using a V-blender for 3 minutes.

TABLE 9

Extended Release Portion W-Z

| | | ER Portion W | | ER Portion X | | ER Portion Y | | ER Portion Z | |
|---|---|---|---|---|---|---|---|---|---|
| | Component | mg/dose | % w/w | mg/dose | % w/w | mg/dose | % w/w | mg/dose | % w/w |
| Granular | DXM | 45 | 11.25 | 45 | 11.25 | 45 | 11.25 | 45 | 11.25 |
| | PSE | 120 | 30 | 120 | 30 | 120 | 30 | 120 | 30 |
| | METHOCEL ™ K100LV[2] | 80 | 20 | 0 | 0 | 160 | 40 | 0 | 0 |
| | METHOCEL ™ K100M[1] | 0 | 0 | 80 | 20 | 0 | 0 | 160 | 40 |
| | Avicel ® PH 102[3] | 151.4 | 37.85 | 151.4 | 37.85 | 151.4 | 37.85 | 151.4 | 37.85 |
| | Aerosil 200 Pharma[6] | 1.6 | 0.4 | 1.6 | 0.4 | 1.6 | 0.4 | 1.6 | 0.4 |
| Extra-granular | Magnesium Stearate | 2 | 0.5 | 2 | 0.5 | 2 | 0.5 | 2 | 0.5 |

[1,2]Available from Colorcon ® (Harleysville, PA)
[3]Available from FMC BioPolymer (Philadelphia, PA)
[6]Available from Evonik Industries (Theodore, AL)

TABLE 10

Extended Release Portion XY

| | | ER Portion XY | |
|---|---|---|---|
| | Component | mg/dose | % w/w |
| Granular | DXM | 45 | 11.25 |
| | PSE | 120 | 30 |
| | METHOCEL ™ K100LV[2] | 0 | 0 |
| | METHOCEL ™ K100M[1] | 80 | 20 |
| | Avicel ® PH 102[3] | 147.18 | 36.79 |
| | Dibasic Sodium Phosphate | 0.34 | 0.085 |
| | Monobasic Sodium Phosphate Monohydrate | 0.18 | 0.045 |
| | Propyl Gallate | 1.3 | 0.325 |
| | Disodium Edetate | 4.0 | 1 |
| Extra-granular | Magnesium Stearate | 2.0 | 0.5 |

[1,2]Available from Colorcon ® (Harleysville, PA)
[3]Available from FMC BioPolymer (Philadelphia, PA)

A 2000 g batch of the extended release portion W—Z can be made as follows. First, all of the ingredients, as shown in Table 9, except the magnesium stearate were added to a Powrex VG25 high shear granulator. 250-550 g of atomized water were added to the granulator bowl while mixing. The wet granulate was then milled using a Fitzmill (available from The Fitzpatrick® Company, Mumbia, India). The milled granulate was then dried to 40° C. in a fluid bed dryer. Then the magnesium stearate and dried granulate were added and blended in a V-blender for 3 minutes.

A 2000 g batch of the extended release portion XY can be made as follows. First, all of the ingredients, as shown in Table 10, except the magnesium stearate can be added to a Powrex VG25 high shear granulator. 250-550 g of an atomized granulation fluid comprising water, EDTA, propylgallate, and phosphate buffer can be added to the granulator bowl while mixing. The wet granulate can then be milled using a Fitzmill (available from The Fitzpatrick® Company, Mumbia, India). Then, the milled granulate can be dried at room temperature in a fluid bed dryer. The magnesium stearate and dried granulate can then be added and blended in a V-blender for 3 minutes.

Bi-Layer Tablets

Next, bi-layer oval tablets comprising an extended release portion and an immediate release portion, as in Examples 1-5 below, can be formed as follows. First, a Carver tablet press (available from Carver Inc., Wabash, Ind.) can be set to deliver a target weight of 440 mg for the immediate release blend A. Then the press can be set to deliver a target weight of 400 mg for the extended release granulated blend W, X, Y, Z, or XY. A compression force of approximately 20 kN can be used to produce tablets of approximately 15 kP hardness.

Examples 1 to 5 can be made according to the table below.

TABLE 11

| | Ex. 1 | Ex. 2 | Ex. 3 | Ex. 4 | Ex. 5 |
|---|---|---|---|---|---|
| IR Portion | A | A | A | A | A |
| ER Portion | W | X | Y | Z | XY |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dosage form comprising:
   a. a first portion comprising a pain reliever selected from the group consisting of acetaminophen, ibuprofen, ketoprofen, diclofenac, aspirin, naproxen, pharmaceutically acceptable salts thereof, and combinations thereof; wherein the first portion is an immediate release portion;
   b. a second portion comprising pseudoephedrine or a pharmaceutically acceptable salt thereof; a chelating agent; dextromethorphan or a pharmaceutically acceptable salt thereof; a basic buffering agent sufficient to achieve a pH of about 6.0 to about 8.0; and a hydrophilic polymer;
      wherein the second portion is an extended release portion;
      wherein the dosage form comprises less than about 0.01%, by weight of the dosage form, methcathinone;
      wherein the dosage form comprises less than about 0.2%, by weight of the dosage form, 10-keto-dextromethorphan.

2. The dosage form of claim 1 wherein the hydrophilic polymer is a hydroxypropyl methylcellulose with a viscosity of from about 10,000 cP to about 250,000 cP.

3. The dosage form of claim 1 wherein the basic buffering agent is selected from the group consisting of meglumine, glycine, sodium carbonate, calcium carbonate, sodium bicarbonate, phosphate buffer, magnesium hydroxide, and combinations thereof.

4. The dosage form of claim 1 wherein the second portion comprises from about 0.5% to about 3% of the chelating agent.

5. The dosage form of claim 4 wherein the chelating agent is selected from the group consisting of EDTA, citric acid, malic acid, tartaric acid, lactic acid, aspartic acid, glutamic acid, lysine, sodium hexametaphosphate, salts thereof, and combinations thereof.

6. The dosage form of claim 1 wherein the second portion further comprises from about 0.1% to about 1% of the antioxidant.

7. The dosage form of claim 6 wherein the antioxidant is selected from the group consisting of ascorbyl palmitate, ascorbic acid, propyl gallate, alpha-tocopherol, butylated hydroxytoluene, butylated hydroxyanisole, tert-butyl hydroquinone, acetyl cysteine, and combinations thereof.

8. The dosage form of claim 1 wherein the dosage form comprises less than about 2 ppm iron.

9. A dosage form comprising:
   a. a first portion comprising a pain reliever selected from the group consisting of acetaminophen, ibuprofen, ketoprofen, diclofenac, aspirin, naproxen, pharmaceutically acceptable salts thereof, and combinations thereof; wherein the first portion is an immediate release portion;
   b. a second portion comprising pseudoephedrine or a pharmaceutically acceptable salt thereof; a stabilizing agent selected from the group consisting of a chelating agent, an antioxidant, and combinations thereof;
      a basic buffering agent sufficient to achieve a pH of about 6.0 to about 8.0; and a hydrophilic polymer;
      wherein the second portion is an extended release portion;
      wherein the dosage form comprises less than about 0.01%, by weight of the dosage form, methcathinone.

10. The dosage form of claim 9, wherein the dosage form comprises a ratio of pseudoephedrine or a pharmaceutically acceptable salt thereof to hydrophilic polymer of from about 0.10 to about 3.0 on a weight basis.

11. The dosage form of claim 9 wherein the antioxidant is selected from the group consisting of ascorbyl palmitate, ascorbic acid, propyl gallate, alpha-tocopherol, butylated hydroxytoluene, butylated hydroxyanisole, tert-butyl hydroquinone, acetyl cysteine, and combinations thereof.

12. The dosage form of claim 11 wherein the second portion comprises from about 0.001% to about 3% of the antioxidant.

13. The dosage form of claim 12 wherein the second portion comprises from about 0.01% to about 1.5% of the antioxidant.

14. The dosage form of claim 12 wherein the second portion comprises from about 0.01% to about 8% of a chelating agent.

15. The dosage form of claim 14 wherein the chelating agent is selected from the group consisting of EDTA, citric acid, malic acid, tartaric acid, lactic acid, aspartic acid, glutamic acid, lysine, sodium hexametaphosphate, salts thereof, and combinations thereof.

16. The dosage form of claim 15 wherein the chelating agent is EDTA.

17. The dosage form of claim 9 wherein the second portion further comprises dextromethorphan or a pharmaceutically acceptable salt thereof.

18. The dosage form of claim 9 wherein the hydrophilic polymer is a hydroxypropyl methylcellulose with a viscosity of from about 10,000 cP to about 250,000 cP.

19. The dosage form of claim 9 wherein the dosage form comprises less than about 0.005%, by weight of the dosage form, methcathinone.

* * * * *